United States Patent [19]

Grace et al.

[11] Patent Number: 5,302,234

[45] Date of Patent: Apr. 12, 1994

[54] SURGICAL CUTTING INSTRUMENT FORMING METHOD

[75] Inventors: Richard L. Grace, Russellville; Jeff Grace, Dover; James Sturtevant, Dardanelle, all of Ark.; Ronald E. Vansaghi, Arlington, Tex.

[73] Assignee: Grace Manufacturing Inc., Russellville, Ark.

[21] Appl. No.: 10,359

[22] Filed: Jan. 28, 1993

[51] Int. Cl.⁵ .................. B44C 1/22; C23F 1/00
[52] U.S. Cl. ........................ 156/640; 156/644; 156/645; 156/661.1; 156/664
[58] Field of Search ............ 156/640, 644, 645, 654, 156/656, 659.1, 661.1, 664; 051/204, 295, 309, 394; 76/12, 21, 25.1, 112; 30/166.3; 428/932

[56] References Cited

U.S. PATENT DOCUMENTS

| | | | |
|---|---|---|---|
| 107,808 | 9/1870 | Phillips | 83/331 X |
| 297,816 | 4/1884 | Ledward | 83/331 X |
| 788,236 | 4/1905 | Bartholomew | 83/331 X |
| 3,045,321 | 7/1962 | McDermott | 29/78 |
| 3,079,669 | 3/1963 | Bryant | 29/78 |
| 4,240,806 | 12/1980 | Frantzen | 51/295 |
| 4,497,686 | 2/1985 | Weglin | 156/651 |
| 5,100,506 | 3/1992 | Sturtevant et al. | 156/645 |

Primary Examiner—William Powell
Attorney, Agent, or Firm—Charles D. Gunter, Jr.

[57] ABSTRACT

The invention relates to a method for manufacturing a sheet metal tool that is not planar, and the tools made from the method. A sheet metal blank has a predetermined design of etching resistant material applied to one surface to define exposed areas separated by resist areas. A layer of etching resistant material is also applied to a second surface of the metal blank which overlies at least the exposed areas on the first surface of the metal blank. The exposed areas on the first surface are then subjected to etchant applied from the first surface of the metal blank through the exposed areas to form a tooth shape with a cutting edge. The formed cutting edge terminates in a sharpened surface in the second surface, protected by the layer of the etching resistant material on the second surface of the metal blank.

10 Claims, 4 Drawing Sheets

SURGICAL CUTTING INSTRUMENT FORMING METHOD

BACKGROUND OF THE INVENTION

1. Field of the Invention

The present invention relates to sheet metal tools that are not planar and are of the type used for cutting and abrading nonlinear surfaces and, specifically, to a method for chemically machining such tools to provide cutting teeth of unique and highly efficient shapes.

2. Description of the Prior Art

Over the millenia, cutting and filing instruments have been the tools of the trade in a wide range of occupations. From art to woodworking, ideas for tool uses crosspollinate between the various tool-using professions. For example, a hacksaw cuts metal, wood or bone, depending on the profession of the user. Each profession, however, may have its own particular demands for tools. For instance, a hacksaw cutting metal may require a blade with different specifications than the surgical version.

Toolmaking has improved and expanded over the years to meet these particular professional demands. Yet, there is a need for better performing cutting tools. Many prior art instruments are punched out of sheet metal. The sheet metal passes through a punch and die, a procedure that imparts holes in the metal. The edges of the holes are then bent to provide the necessary "set" to make the desired cutting edge profile, such as a tooth.

These state-of-the-art instruments lack a preferred degree of sharpness. This is partially the result of the cutting edges being formed by the ragged die cuts in the metal blank. More expensive instruments have ground edges, however, this grinding process is limited in both application and possible tooth arrangements because the grinding well or broach is required to enter and exit the tooth in a straight line. As a result, the available tooth patterns are relatively simple and linear.

Because of the high cost of tooling and grinding, attempts were made to manufacture sheet metal instruments by chemical etching. These endeavors resulted in end products that tended to do more rubbing than cutting, primarily due to the lack of side, frontal and/or top relief in the etched individual tooth patterns.

The method of toolmaking revealed in U.S. Pat. No. 5,100,506 is a major improvement in toolmaking. This patent discloses a method of chemically machining tools to provide sharp cutting teeth of unique and highly efficient shapes. The method works effectively to machine cutting edges on planar sheet metal objects, such as flat rasps, files and saw blades. The improvements were not specifically directed, however, toward sheet metal objects that are not planar.

The above prior art does not specifically address the problems of making cutting tools that are not planar. Such instruments perform a variety of functions, typically smoothing and cutting nonlinear surfaces. The prior art instruments with cutting edges on curved surfaces may use no teeth, for example, an acetabular reamer with punched holes for cutting edges. Each hole in the acetabular reamer is individually drilled, countersunk and set from the inside of the hemisphere. This produces an instrument that easily clogs and dulls. Therefore, new methods are needed to produce better cutting tools for curved surfaces.

Surgical procedures have been performed using tools since at least the neolithic era. Surgical instruments frequently evolve from the tools of other professions, like cutting blades and scissors common to both medicine and barbering. Other instruments derive from the saws, rasps, gouges and files from woodworking and metalworking.

Surgical procedures often involve cutting and filing tough tissue such as bone and cartilage. In hip implant surgery, both the head of the femur or the "ball" and acetabulum or cup shaped pelvic socket are removed and replaced with artificial counterparts. To attach the prosthetic head, a longitudinal cavity must be reamed down the femur to anchor the stem of the head using a T-handle femoral shaft reamer or broach. After replacing the head, the surgeon deepens the acetabulum by reaming or gouging until it accepts the acetabular prosthesis.

These prior art surgical instruments have several disadvantages. They often require extensive hand finishing to form the cutting edges. They dull quickly and are heavy. Dull cutting instruments roughly grind and scrape rather than cut the tissue. In surgery, smooth cutting reduces the risks of sepsis or infection. Dull instruments also require more force to remove the tissue from its location. For example, disposable scalpel blades with reusable handles are preferred over reusable scalpels. The cutting edge of a reusable scalpel dulls quickly, thereby requiring constant sharpening for efficient use. Since a surgical procedure cannot be interrupted to sharpen the cutting edge, many reusable scalpels are often needed. Heavy weight instruments generate heat and are fatiguing to use.

The prior art surgical instruments are reusable and therefore require designs for easy cleaning of tissue. This requirement hinders the design of more effective cutting surfaces. Reusable instruments are immediately cleaned and sterilized to prevent degradation of the instrument and prepare them for reuse. Tissue traps and lodges within complex cutting edges, thereby requiring hand cleaning to ensure adequate tissue removal. The instruments must first soak in germicidal detergent solutions which do not always effectively kill all infectious agents, thereby presenting a risk to the worker who cleans the instruments. Chlorine solutions such as bleach effectively kill infectious agents but degrade the metal in the instruments. Ultrasonic cleaning after hand cleaning helps remove much of the trapped tissue, however, the problems of infectious agents still exist. Sterilizing the equipment prior to cleaning is not recommended. The tissue degrades the metal. Further, sterilizing before cleaning hardens the tissue on the instrument making it difficult to remove.

Sharper and lighter surgical instruments are thus desirable. Sharper instruments cut tissue smoothly with less force rather than grinding or scraping it. Lighter instruments must be strong enough to withstand the forces placed on the instrument during surgery, such as reaming out the femur during hip replacement surgery. The lighter sheet metal cannot deform or break during punching and forming the cutting edges.

Chemically machined instruments from sheet metal use lighter sheet metal. The sheet metal is lighter, yet strong, resisting deformation and breakage. Chemically machined edges are sharper and require less hand finishing. Since thinner and lighter metals are used, the tools can be disposable.

It is an object of the invention to provide an improved chemical machining method for manufacturing cutting tools that are not planar which overcomes the previously mentioned shortcomings. Another object of the invention is to provide improved cutting tools for nonlinear surfaces.

Another object of the invention is to provide a greater array of cutting edges or tooth designs for such tools that cut materials more efficiently than the presently available designs.

Another object of the invention is to provide improved sheet metal cutting tools that are not planar and a method of manufacture that eliminates the necessity of grinding the cutting edges, the use of expensive dies and fixtures or extensive hand finishing of the instrument.

Another object of the invention is to provide effective and inexpensive cutting tools that are not planar for surgical use.

SUMMARY OF THE INVENTION

The manufacturing method of the invention is used to form a nonplanar, sheet metal tool, such as an abrading or cutting tool. The tool is manufactured from a metal blank with two surfaces, a first surface and an opposing second surface. A predetermined design of etching resistant material is applied to the first surface of the metal blank, defining exposed areas separated by resist areas. A layer of etching resistant material is applied to the second surface of the metal blank which overlies at least the exposed areas on the first surface of the metal blank. The exposed areas on the first surface of the metal blank are subjected to etching treatment to form a cutting edge, such as a tooth shape. The etching treatment is applied solely from the direction of the first surface of the metal blank, whereby the formed cutting edges terminate in sharpened surfaces in the second surface and are protected by the layer of etching resistant material on the second surface of the metal blank. The tool can be given a nonplanar shape at any point in the manufacturing process, i.e., either before or after the resist-/etching steps.

Preferably, the metal blank is put into a holder so that the surface being etched faces the etching apparatus. During the etching treatment, the holder moves to evenly distribute the etchant onto the metal blank. Most preferably, the etching treatment is applied to the metal blank by using at least one nozzle connected to the etching apparatus.

Preferably, the exposed areas on the first surface of the metal blank form a tooth shape and an associated tooth opening in each of the exposed areas during the etching treatment. Each tooth shape is preferably formed with a cutting edge opposite a tooth base. At least selected teeth are bent along their respective bases to bring their respective cutting edges away from the second surface of the metal blank.

In certain embodiments, the teeth are formed having cutting edges opposite a tooth base and opposing side edges. In order to reduce stress at the base region, the area proximate the tooth side edges can be etched equally from the direction of both the second surface of the metal blank and the first surface. The cutting edge of the tooth continues to be etched from the direction of the first surface only.

In another embodiment of the invention, the previously described resist design alternates on the first and second surfaces of the metal blank. Alternating exposed areas on the first surface are overlaid by a layer of resist on the second surface and alternating exposed areas on the second surface are overlaid by a layer of resist on the first surface. The exposed areas on the first surface of the metal blank are then subjected to etching treatment through the exposed areas to form a tooth shape and an associated tooth opening as previously described. Then the exposed areas on the second surface of the metal blank are subjected to etching treatment through the exposed areas to form a tooth shape, with the etching treatment being applied from the opposite direction of the etching treatment applied to the first surface.

Those teeth formed with their sharpened surfaces in the first surface are bent along their respective bases to bring their respective cutting edges away from the first surface of the metal blank. Teeth formed with their sharpened surfaces in the second surface are bent along their respective bases to bring their respective cutting edges away from the second surface of the metal blank.

A sheet metal file with a three dimensional, nonplanar structure is made by the method of the invention. The sheet metal file of the invention includes a plurality of chemically etched teeth. Any given tooth is etched solely from one side of a metal blank. Alternate teeth or groups of teeth may be etched from opposite sides to create a file that cuts on both sides. Each tooth is bent at its base to bring the cutting edge of the tooth above the surface of the file.

Additional effects, features and advantages will be apparent in the written description that follows.

DETAILED DESCRIPTION OF THE INVENTION

The present invention chemically etches cutting and filing instruments with teeth and slots for material removal. Chemical etching permits greater flexibility in tooth design, arrangement and selection of material. By design, instruments made by the method of the invention are thinner, lighter and sharper, as well as flexible or rigid, depending on the use. The instruments are less likely to clog than those made with the prior art techniques. These instruments can also be disposable.

The following terms used in this disclosure have these meanings: "nonplanar" refers to any three dimensional structure or shape that is not planar, for example, curved, cubical, box-like, spoon-like, hemispherical, cylindrical, ellipsoid, and the like; "tooth" refers to the cutting surface formed by the method of the invention and contains at least one cutting edge; "etching treatment" refers the act of etching; and "etchant" refers to the fluids used for etching.

Chemical etching techniques are known in the art for making devices, tools or instruments having cutting teeth such as files, rasps, saw blades, and the like. Such techniques are described in U.S. Pat. No. 4,240,806, issued Dec. 23, 1980 and U.S Pat. No. 3,045,321, issued Jul. 24, 1962, the disclosure of which is incorporated herein by reference. A metal blank with two surfaces, a first surface and an opposing second surface is used for making the instruments. Interior and exterior or front and back surfaces are two examples of the first and second surfaces. The metal blank has areas that are to form cutting surfaces, such as teeth, ridges or other cutting elements. The first surface of the metal blank is selectively coated with a resist material to prevent the etching fluid from contacting and acting on the blank surface. Other areas of the first surface are left exposed for the etching treatment. The second surface of the metal blank is coated with a resist material that overlies at least the exposed areas on the first surface of the metal blank. The etching fluid first acts on the surface areas unprotected by the resist material, and as the etching proceeds, the material not protected by the resist is removed.

The general family of etching fluids and resist materials used for the purposes of the present invention are available commercially from a number of sources. Both wet film and dry film resists are acceptable for use in practicing the method of the invention. The selection of a particular resist depends on the shape of the metal blank and the desired detail of the cutting edges. For a planar blank that does not require a limited fineness of cutting edge detail, a wet resist screened onto the blank over an adhesive cut-out or stencil is preferred. The dry film resist is preferred, however, for a nonplanar blank or the formation of finely detailed cutting edges. The dry film resist has an increased stretchiness and adhesion that allows it to be applied to a planar blank before forming a nonplanar blank. The stretchable nature of such dry film resists allows them to easily fit the curved, nonplanar articles being etched without inserting extraneous gaps, tears or bubbles that could introduce improper etching designs.

The design of the resist material which is coated on the blank varies according to the character of the cutting elements that are desired. The designs can be made by hand or computer generated. Using a computer allows the generation of customized designs for the instrument and its particular use which may be complex, intricate, patterned and/or random. For example, patterned designs are preferable for hemispherical rasps.

Preferably, the cutting surface forms a tooth with a cutting edge and a base. The actual shape of the tooth can refer to a variety of shapes, such as shark toothed, flat toothed, jagged, and the like. The tooth may also be slightly smaller on one side than the other.

The cutting elements of the invention may be formed on any material that is suited to etching treatment. Most of current suitable materials are metals. Steels of various compositions and hard alloys are currently best suited for use as the blank material where long life and adaptability to the cutting of hard substances is required. For example, stainless steel sheets (Rc 30/55, 300/400 Series Stainless Steel), mild steels adapted to be hardened subsequent to the etching treatment and surgical steels can be used as the blank or body of the abrading devices of the invention. Thin metal sheets, such as steel, are preferred when making surgical instruments. The metal must be capable of making nonplanar instruments, either by shaping in a die, melting and molding, milling or lathing. The metal must be strong enough in use to cut the desired material, yet not break or deform, a trait critical for disposable surgical instruments. The surface does not have to be continuous, rather it can have one or more gaps. See, e.g., FIG. 4. The nonplanar surface can also be hollow. See, e.g., FIG. 9.

Although forming the nonplanar shape from the planar metal blank can be done at any time during the method of the invention, the best mode depends on the type of instrument. For hemispherical instruments, the shaping preferably occurs after adding the resist and prior to the etching treatment. For instruments of the type shown in FIGS. 4–6, the nonplanar shaping preferably follows the etching treatment.

Figure 1:
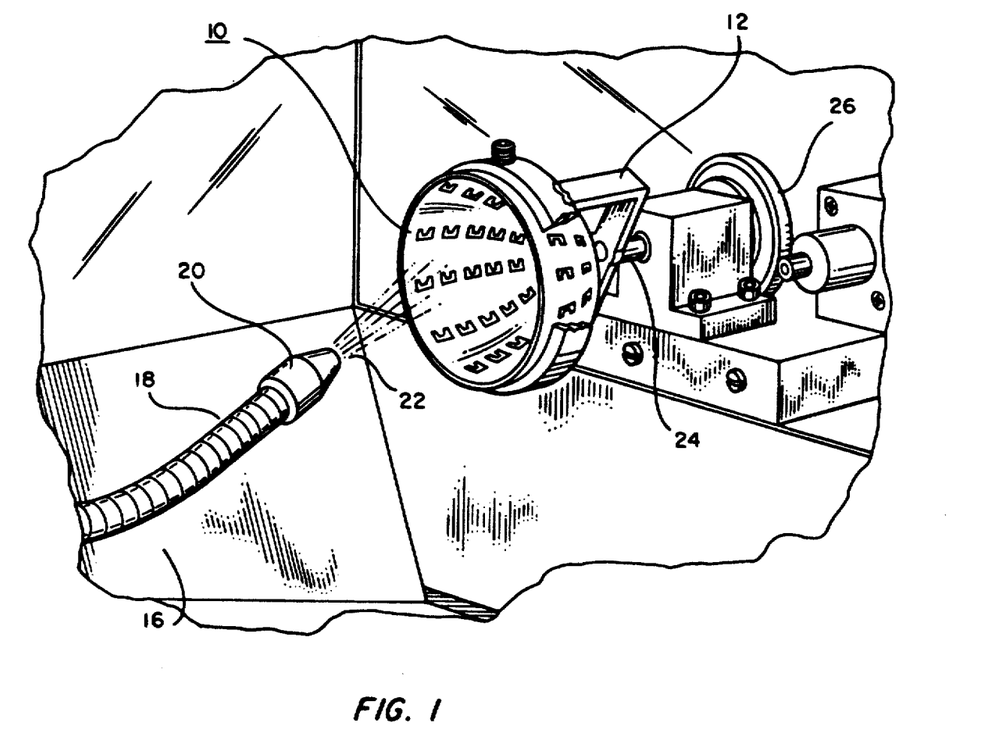
FIG. 1 is a view of one method of the invention during etching.

Preferably, the sheet metal blank 10 is placed in a holder 12 after applying the resist design to the blank 10 as shown in FIG. 1. The surface to be etched faces at least one treatment apparatus 16 connected to some type of etching apparatus. During chemical etching, the holder 12 may move to evenly distribute the etchant. Most preferably, the holder 12 rotates at a constant velocity, using a rotatable shaft 24 connected to a drive means 26 especially for hemispherical blanks 10.

Preferably, at least one treatment applicator 16 applies the etchant to the blank. Preferably, the treatment applicator 16 has a supply line 18, such as a tube, to carry the etchant and a jet or nozzle 20 at one end. The nozzle 20 should have at least one orifice 22 from which the etchant is directed. Most preferably, the etchant is supplied through the treatment applicator 16 supply line 18 and sprayed from a nozzle 20 onto the sheet metal blank 10. The etchant may be applied with the nozzle 20 stationary or moving, whichever gives a even etchant coating for the particular shape of the blank 10.

The etched tools formed by the method of the invention have cutting teeth generally used for shaping or reaming that are preferably bent along the base away from the surface of the blank. Unlike prior art tools, the instruments made by the method of the invention do not readily clog, because removed material passes easily through the instrument's openings. The instruments of the invention can be used as either hand tools or power tools. They may attach to a support mechanism or an arm, for instance, a handle, chuck, brace, and the like.

Figures 2, 3, 4, 5, 6:
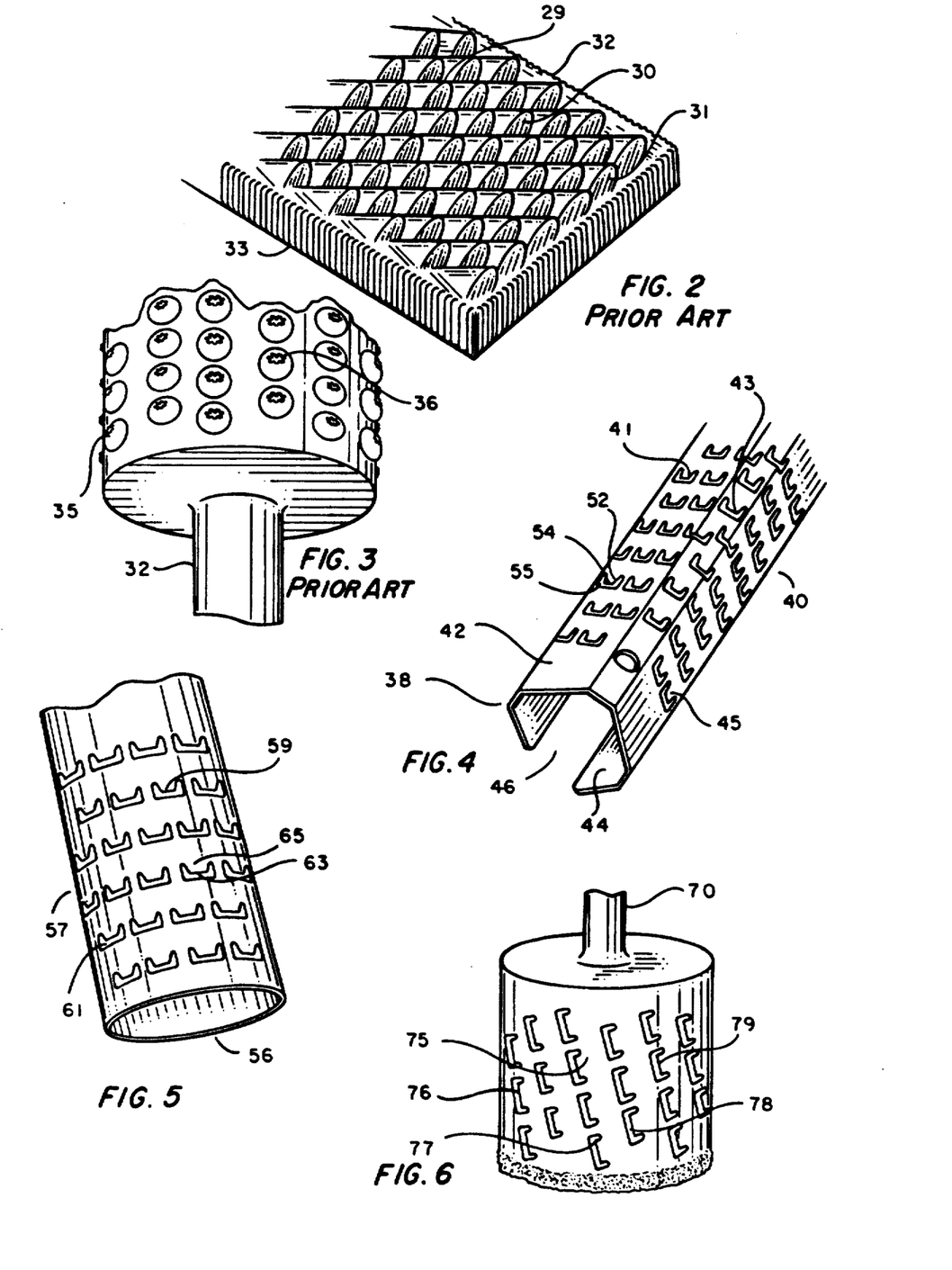
FIG. 2 is a close-up view of part of a planar wood rasp of the prior art.
FIG. 3 is a sheet metal rasp from the prior art.
FIG. 4 is a square, oblong rasp made from the method of the invention.
FIG. 5 is a close-up View of a cylindrical rasp made from the method of the invention.
FIG. 6 is a cylindrical rasp made from the method of the invention.

FIG. 2 shows a close-up view of part of a planar wood rasp from the prior art. The teeth 29, 30, 31 on the top and the ridges 32, 33 along the side are relatively dull. Both the shape and high angle of the teeth 29, 30, 31 give them a scraping and gouging action. Making this type of rasp requires using thick slabs of heavy steel. A hemispherical version would be extremely heavy and expensive and would not give the desired cutting action.

The ARCO ROTO-RASP shown in FIG. 3 is the most primitive form of a nonplanar sheet metal rasp. The sheet metal is crudely punched to produce broken edges or teeth 35, 36 for cutting. This model is attached to an arm or chuck 32. These tools are lightweight, inexpensive, fast cutting and easily manufactured in a variety of useful shapes and sizes. Their cutting actions are very rough, shredding rather than cutting, making them inappropriate for surgical use.

FIG. 4 shows one of the nonplanar rasps of the invention. This square rasp is box-like with a square end 38 and an oblong end 40 perpendicular to the square end 38. The rasp has an outside surface 42 and an opposite inside surface 44. The metal is not continuous but has a gap 46. The rasp may attach to a handle for easy use, such as cutting a trench. The teeth 41, 43, 45 have a base 52, a cutting edge 54, and tooth openings 55.

Other examples of the invention are the cylindrical rasps presented in FIGS. 5 and 6. FIG. 5 is a close-up view of a cylindrical rasp with a round 56 end and an oblong side 57 perpendicular to the plane of the circle. The teeth 59, 61 have cutting edges 63 and bases 65. This rasp could easily adapt to form a tapered cutting instrument with one round end wider than the opposite round end. FIG. 6 shows a short round rasp attached to a chuck 70 for reaming or smoothing a hole. Although the tooth design has shorter teeth 75, 76 and larger openings 77, 78, the cutting edges 79 remain unchanged. This tool could be adapted for neurosurgical uses, such as a trephine.

Figure 7:
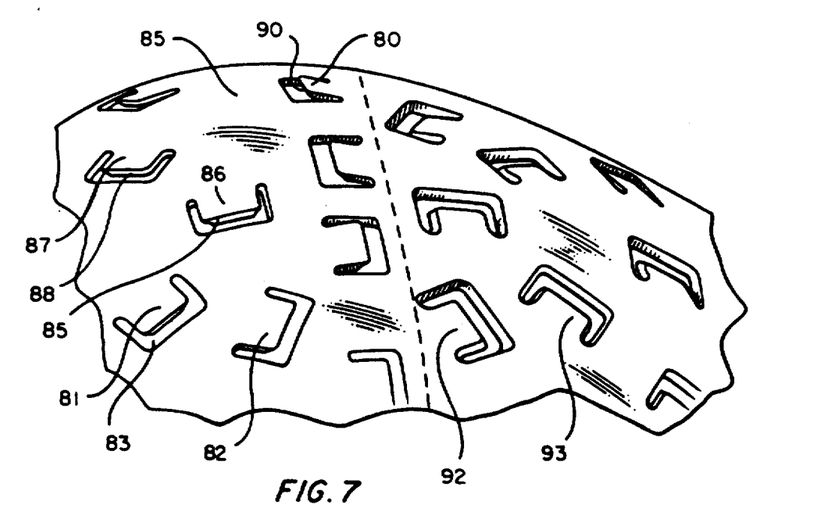
FIG. 7 is a schematic drawing of the area on the top of a hemispherical rasp, demonstrating the tooth design for concave and convex surfaces.

FIG. 7 pictures an area near the top of a hemispherical rasp. The teeth 80, 81, 82 and openings 83 to the left of the dashed line illustrate a shaping and smoothing tool for concave surfaces such as found in an acetabulum. The teeth 80, 81, 82 are etched from the inside surface of the hemisphere with the image of the teeth on the inside surface and a solid coat of resist on the outside surface 85. Each tooth 80, 81, 82 has a base 86, 87 and a cutting edge 88, 89, 90. The tooth openings 83 are along the cutting edge 88, 89, 90 and the sides of the tooth 80, 81, 82. The etched teeth then are bent outward away from the outside surface 85 and toward the opposite inside surface.

The teeth 92, 93 to the right of the dashed line illustrate a convex surface tool. They are etched from the outside surface 85 of the hemisphere instead of the inside surface. The image of the teeth is on the outside surface 85 and a solid coat of resist is on the inside surface. The etched teeth 92, 93 are bent inward away from the inside surface and toward the opposite outside surface 85.

Figures 8A, 8B:
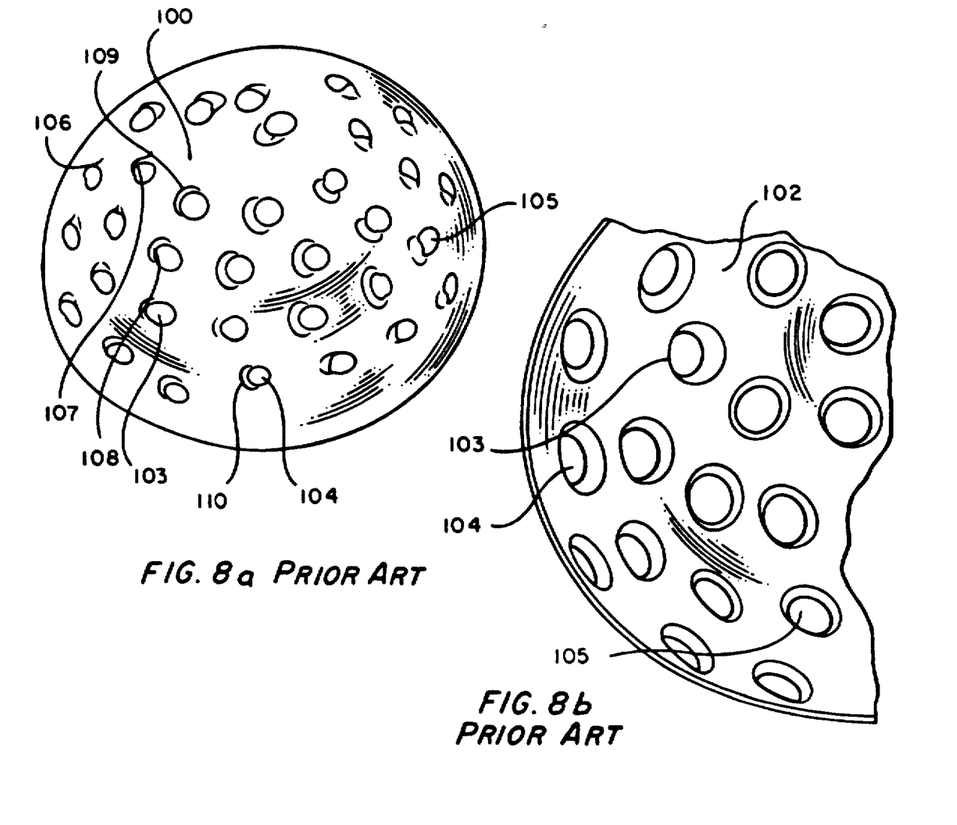
FIG. 8a is a view of the exterior surface of an acetabular reamer from the prior art.
FIG. 8b is a view of the interior surface of an acetabular reamer from the prior art.

A prior art reusable acetabular reamer is shown in FIGS. 8a and 8b. FIG. 8a views the outside surface 100 while FIG. 8b views the inside surface 102. Each hole 103, 104, 105 is individually drilled, countersunk and set to form a scoop 106 from the inside surface 102 of the hemisphere. The cutting edges 107, 108 form scoop-like teeth 109, 110 and are crude and quite dull.

Figure 9:
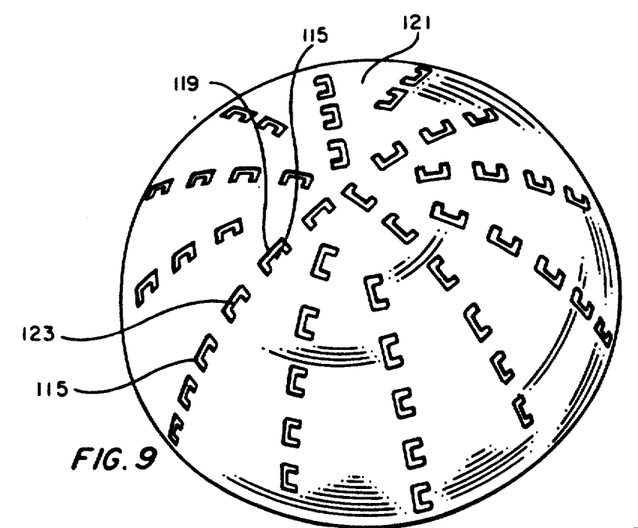
FIG. 9 is a view of the exterior surface of an acetabular reamer made from the method of the invention.

FIG. 9 demonstrates an acetabular reamer made from the method of the invention. Teeth 115 are bent along the base 117 opposite the cutting edge 119 and away from the outside surface 121. The tooth openings 123 are rounded to reduce clogging. The reamer can fit onto the end of an arm like a handle or brace during application. After finishing, the reamer can be removed and discarded if desired.

Figures 10, 11:
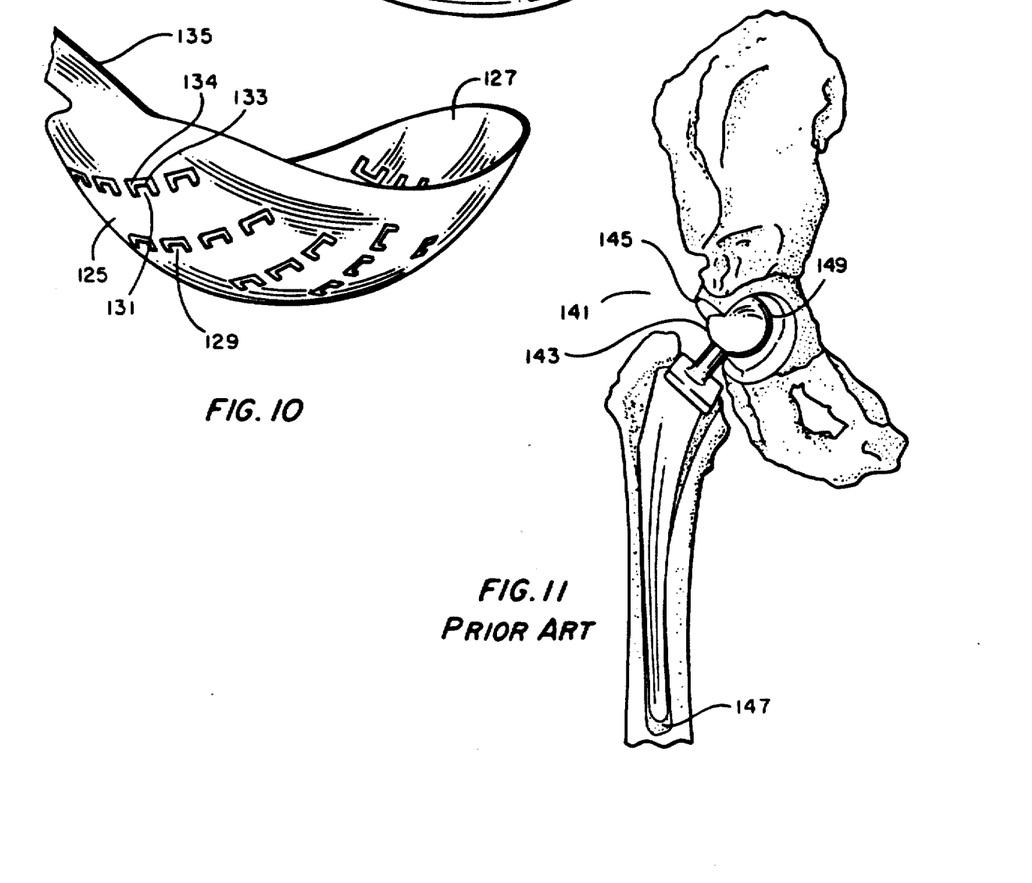
FIG. 10 is a spoon-shaped rasp for concave surfaces, made from the method of the invention.
FIG. 11 is a side view of a human hip, partially in section, showing a hip prosthetic implant in place within the femur and acetabular socket.

FIG. 10 exhibits another configuration of the invention. This spoon-shaped rasp is designed for curved, concave surfaces. The rasp has an outside surface 125 and an inside surface 127. The teeth 129 are similar to the acetabular reamer, having a base 131 and a cutting edge 133. The tooth opening 134 is rounded. The rasp attaches to a handle 135 for easy use. This tool can be adapted for surgical uses, perhaps for reconstructive surgery.

FIG. 11 illustrates the type of cavities that can be made using the tools produced by the method of the invention through the example of a human hip prosthesis 141 from a side view partially in section. The head of the prosthetic femur 143 lies within the femur and within the prosthetic acetabulum 145. An orthopedic surgeon reams a longitudinal cavity 147 into the femur for receiving the prosthesis. The surgeon prepares the acetabulum 149 to receive the acetabular prosthesis 145, by reaming or another method of cutting out the socket. A smoother cavity fits the prosthesis better and lessens the chance of sepsis. If the prosthesis fits poorly, it may loosen over time and cause bone erosion. Bone erosion can lead to tissue reactions, which can cause further bone erosion. The joint itself can come out of alignment and/or is damaged beyond repair.

The method of the invention produces instruments with many advantages. The method produces instruments with a wide range of uses in a number of professions, such as slow speed router-shaper bits for woodworking. The instruments save time and effort by conforming to curved surfaces and cutting the surfaces smoothly and quickly. Nonplanar instruments can readily replace crude gouging and chiseling instruments, especially those employed in surgery.

The method of the invention readily adapts to make specialized instruments that fulfill the particular professional demands. The method works well on both nonplanar and planar surfaces. The method makes cutting and filing instruments in a wider variety of shapes, weights and sizes to fit the job, such as the many different shapes previously disclosed. Carpenters may want heavier, reusable instruments. Surgeons and hospitals may want light, sharp, disposable instruments. The method of the invention allows the easy and exact manufacture of cutting tools. Instruments conform to the type of action, such as a push stroke or a pull stroke.

The method of the invention produces better cutting surfaces. The instruments have more teeth and a wider variety of cutting edges and tooth distribution, such as fine tooth and coarse tooth. The teeth conform to the shape of the instrument instead of the chordal or flat tooth surface that is used in state-of-the-art cutting surfaces. For instance, a carpenter may require one type of tooth and tooth pattern, while a surgeon may want another. Surgical subspecialties like plastic and reconstructive surgery, neurosurgery or orthopedic surgery may each prefer customized types of teeth depending on the type of tissue that is being cut.

The instruments can use a common handle to hold specific cutting tools for a procedure. After use, the cutting tool can be removed and discarded if so desired. It is not necessary to replace the whole instrument.

While the invention is shown in only one of its forms, it is not thus limited but is susceptible to various changes and modifications without departing from the spirit and scope of the invention.

What is claimed is:

1. A method of manufacturing a nonplanar, sheet metal tool form from a planar metal blank of the type having two surfaces with a first surface opposing a second surface, the method comprising the steps of:
   applying to the first surface of the metal blank a predetermined design of etching resistant material defining exposed areas separated by resist areas;

applying a layer of etching resistant material to the second surface of the metal blank which overlies at least the exposed areas on the first surface of the metal blank;

shaping the metal blank into a nonplanar shape; and subjecting the exposed areas on the first surface of the metal blank to an etchant to form a surface with a cutting edge, the etchant being applied solely from the first surface of the metal blank, whereby the cutting edges so formed terminate in sharpened surfaces in the second surface and are protected by the layer of etching resistant material on the second surface of the metal blank.

2. A method of manufacturing a nonplanar, sheet metal tool from a planar metal blank of the type having two surfaces with a first surface opposing a second surface, the method comprising the steps of:

applying to the first surface of the metal blank a predetermined design of etching resistant material defining exposed areas separated by resist areas;

applying a layer of etching resistant material to the second surface of the metal blank which overlies at least the exposed areas on the first surface of the metal blank;

shaping the metal blank into a nonplanar shape;

placing the metal blank into a holder;

providing a treatment applicator for applying an etchant and orienting the applicator so that the first surface faces the applicator;

subjecting the exposed areas on the first surface of the metal blank to an etchant to form a surface with a cutting edge, the etchant being applied solely from the first surface of the metal blank and moving at least one of the holder and treatment applicator to evenly distribute the etchant onto the metal blank; and whereby the cutting edges so formed terminate in sharpened surfaces in the second surface and are protected by the layer of etching resistant material on the second surface of the metal blank.

3. A method of manufacturing a nonplanar, sheet metal tool from a planar metal blank of the type having two surfaces with a first surface opposing a second surface, the method comprising the steps of:

applying to the first surface of the metal blank a predetermined design of etching resistant material defining exposed areas separated by resist areas;

applying a layer of etching resistant material to the second surface of the metal blank which overlies at least the exposed areas on the first surface of the metal blank;

shaping the metal blank into a nonplanar shape;

placing the metal blank into a holder;

providing a treatment applicator for applying an etchant and orienting the applicator so that the first surface faces the applicator;

subjecting the exposed areas on the first surface of the metal blank to the etchant to form teeth having cutting edges, the etchant being applied solely from the first surface of the metal blank and moving at least one of the holder and treatment applicator to evenly distribute the etchant onto the metal blank;

whereby the teeth so formed terminate in sharpened surfaces in the second surface and are protected by the layer of etching resistant material on the second surface of the metal blank; and bending at least selected teeth so formed to bring their respective cutting edges away from the second surface of the metal blank.

4. The method of claim 3, wherein each tooth that is formed has a cutting edge opposite a tooth base and opposing side edges which terminate in a root region of the tooth, the method further comprising the steps of etching the area proximate the root region of each tooth equally from the directions of both surfaces of the metal blank.

5. The method of claim 3, wherein the etching resistant material is a wet film resist.

6. The method of claim 3 wherein the etching resistant material is a dry film resist.

7. The method of claim 6 wherein the dry film resist is applied by the method comprising the steps of:

fitting the resist to the first and second surfaces of the metal blank; and exposing the first and second surfaces of the metal blank in only the defined exposed areas of the predetermined design of the dry film resist.

8. A method of manufacturing a nonplanar, sheet metal tool from a planar metal blank of the type having two surfaces with a first surface opposing a second surface, the method comprising the steps of:

applying to the first surface of the metal blank a predetermined design of etching resistant material defining exposed areas separated by resist areas;

applying a layer of etching resistant material to the second surface of the metal blank which overlies at least the exposed areas on the first surface of the metal blank;

placing the metal blank into a holder;

providing a treatment applicator for applying an etchant and orienting the applicator so that the first surface faces the applicator;

subjecting the exposed areas on the first surface of the metal blank to the etchant to form teeth having cutting edges, the etchant being applied solely from the first surface of the metal blank and moving at least one of the holder and treatment applicator to evenly distribute the etchant onto the metal blank;

whereby the teeth so formed terminate in sharpened surfaces in the second surface and are protected by the layer of etching resistant material on the second surface of the metal blank;

shaping the metal blank into a nonplanar shape after subjecting the exposed areas to the etchant; and bending at least selected teeth so formed to bring their respective cutting edges away from the second surface of the metal blank.

9. A method of manufacturing a nonplanar, sheet metal tool from a planar metal blank of the type having two surfaces with a first surface opposing a second surface, the method comprising the steps of:

applying to the first surface of the metal blank a predetermined design of etching resistant material defining exposed areas separated by resist areas;

applying a layer of etching resistant material to the second surface of the metal blank which overlies at least the exposed areas on the first surface of the metal blank;

shaping the metal blank into a nonplanar metal blank;

placing the nonplanar metal blank into a holder;

providing a treatment applicator for applying an etchant and orienting the applicator so that the first surface faces the applicator;

subjecting the exposed areas on the first surface of the nonplanar metal blank to the etchant to form teeth having cutting edges, the etchant being applied solely from the first surface of the nonplanar metal blank and moving at least one of the holder and treatment applicator to evenly distribute the etchant onto the nonplanar metal blank;

whereby the teeth so formed terminate in sharpened surfaces in the second surface and are protected by the layer of etching resistant material on the second surface of the nonplanar metal blank; and bending at least selected teeth so formed to bring their respective cutting edges away from the second surface of the nonplanar metal blank.

10. A method of manufacturing a nonplanar, sheet metal tool from a planar metal blank of the type having two surfaces with a first surface opposing a second surface, the method comprising the steps of:

applying to the first surface of the metal blank a predetermined design of etching resistant material defining exposed areas separated by resist areas;

applying a layer of etching resistant material to the second surface of the metal blank which overlies at least the exposed areas on the first surface of the metal blank;

alternating the previously described resist design on the first and second surfaces so that alternating exposed areas on the first surface are overlaid by a layer of resist on the second surface and so that alternating exposed areas on the second surface are overlaid by a layer of resist on the first surface;

shaping the metal blank into a nonplanar shape;

placing the metal blank into a holder;

providing a treatment applicator for applying an etchant and orienting the applicator so that the first surface faces the applicator;

subjecting the exposed areas on the first surface of the metal blank to etchant to form teeth having cutting edges, the etchant being applied solely from the first surface of the curved metal blank and moving at least one of the holder and treatment applicator to evenly distribute the etchant onto the metal blank;

whereby the cutting edges so formed terminate in sharpened surfaces in the second surface and are protected by the layer of etching resistant material on the second surface of the metal blank;

removing the metal blank from the holder and replacing the metal blank into a holder so that the second surface faces the treatment applicator;

subjecting the exposed areas on the second surface of the metal blank to etchant to form teeth having cutting edges, the etchant being applied solely from the second surface of the curved metal blank and moving at least one of the holder and treatment applicator to evenly distribute the etchant onto the metal blank;

whereby the cutting edges so formed terminate in sharpened surfaces in the first surface and are protected by the layer of etching resistant material on the first surface of the metal blank; and bending at least selected teeth so formed along their respective bases to bring their respective cutting edges away from the surface of the metal blank.

* * * * *